US012623046B2

(12) United States Patent
Murugesan et al.

(10) Patent No.: US 12,623,046 B2
(45) Date of Patent: May 12, 2026

(54) COLOR-CHANGING AUTOMOTIVE CABIN INTERIORS UTILIZING PHOTOPLETHYSMOGRAPHY TECHNOLOGY

(71) Applicant: FCA US LLC, Auburn Hills, MI (US)

(72) Inventors: Sathishkumar Murugesan, Salem District (IN); Shweta Kulkarni, Pune (IN)

(73) Assignee: FCA US LLC, Auburn Hills, MI (US)

( * ) Notice: Subject to any disclaimer, the term of this patent is extended or adjusted under 35 U.S.C. 154(b) by 323 days.

(21) Appl. No.: 18/457,602

(22) Filed: Aug. 29, 2023

(65) Prior Publication Data

US 2025/0073416 A1    Mar. 6, 2025

(51) Int. Cl.
| | |
|---|---|
| *G02B 26/00* | (2006.01) |
| *A61M 21/00* | (2006.01) |
| *B60R 13/02* | (2006.01) |
| *G02F 1/00* | (2006.01) |
| *G09G 3/19* | (2006.01) |

(52) U.S. Cl.
CPC ............. *A61M 21/00* (2013.01); *B60R 13/02* (2013.01); *A61M 2021/0044* (2013.01); *A61M 2205/3303* (2013.01); *A61M 2205/3313* (2013.01); *A61M 2209/088* (2013.01)

(58) Field of Classification Search
CPC .......... F21V 14/003; G02F 1/009; G02F 1/15; G02F 1/155; G02F 1/153; G02F 1/1503; G02F 1/1506; G02F 1/157; G02F 1/0121; G02F 1/03; G02F 1/0018; G02B 26/004; G02B 26/001; G09G 3/19

USPC ....... 359/288, 265–277, 245, 247, 242, 254, 359/240, 250, 253, 315, 318, 321; 345/49, 105; 348/817; 250/70; 438/929
See application file for complete search history.

(56) References Cited

U.S. PATENT DOCUMENTS

| | | | | |
|---|---|---|---|---|
| 6,816,149 | B1 * | 11/2004 | Alsleben | ............. G06F 3/03543 |
| | | | | 374/161 |
| 7,278,369 | B2 | 10/2007 | Kelley et al. | |
| 2017/0255264 | A1 * | 9/2017 | Dash | ................... G06F 3/03547 |
| 2018/0065453 | A1 * | 3/2018 | Gaddis | .................. G02F 1/0121 |

FOREIGN PATENT DOCUMENTS

| | | | | |
|---|---|---|---|---|
| CN | 115782792 | A | * | 3/2023 |
| JP | 2019-534817 | A | | 12/2019 |

OTHER PUBLICATIONS

Translation of CN 115782792 (Year: 2023).*

* cited by examiner

*Primary Examiner* — Dawayne Pinkney
(74) *Attorney, Agent, or Firm* — Jeremy J. Klobucar

(57) ABSTRACT

A vehicle including a plurality of interior panels that include an outer decorative layer formed of a material that includes a thermochromic coloring agent. A physiologic condition monitoring device monitors various physiologic conditions of a driver of the vehicle, and based on the physiologic conditions of the driver, a temperature of the thermochromic coloring agent can be changed to change a first color of the thermochromic coloring agent to a second and different color to influence the physiologic condition of the driver.

18 Claims, 6 Drawing Sheets

| Heating Temperature | Temperature Increasing | Temperature Cooling After Rising Temperature 23°C |
|---|---|---|
| 60°C | dark red | dark red |
| 65°C | light red | red |
| 70°C | dark orange | red |
| 75°C | light orange | red |
| 80°C | light yellow | pink |
| 85°C | dark yellow | dark yellow |

FIG. 5

COLOR-CHANGING AUTOMOTIVE CABIN INTERIORS UTILIZING PHOTOPLETHYSMOGRAPHY TECHNOLOGY

FIELD

The present disclosure relates to color-changing automotive cabin interiors utilizing photoplethysmography technology.

BACKGROUND

This section provides background information related to the present disclosure which is not necessarily prior art.

Vehicle collisions occur due to a variety of reasons including careless operation of the vehicle, violation of traffic laws, and various personal physiological factors including anxiety, nervousness, stress, and drowsiness. With respect to drowsiness, various driver sleep detection systems have been developed where, for example, a vehicle camera monitors a driver's eye condition. If the detected driver's eye condition is indicative of the driver potentially being asleep, an alarm system may be activated to awake the driver. The drawback to such a system, however, that the system can only detect whether a driver is asleep and cannot detect other physiological factors affecting the driver such as anxiety, nervousness, and stress.

SUMMARY

This section provides a general summary of the disclosure and is not a comprehensive disclosure of its full scope or all of its features.

According to a first aspect of the present disclosure, there is provided a vehicle including a body defining a vehicle cabin. The vehicle includes a plurality of interior panels located in the vehicle cabin that include an outer decorative layer formed of a material that includes a thermochromic coloring agent, a backing layer, and a flow path sandwiched between the outer decorative layer and the backing layer; a physiologic condition monitoring device configured to generate signals indicative of various physiologic conditions of a driver of the vehicle; a master controller in communication with the monitoring device that is configured to receive and analyze the signals generated by the monitoring device; and a fluid source in fluid communication with the flow path, the fluid source having a fluid that is configured to flow between the fluid source and the flow path, wherein based on analysis by the master controller of the signals indicative of the physiologic condition of the driver of the vehicle generated by the monitoring device, the fluid in the flow path is configured to selectively heat and cool the thermochromic coloring agent to change a first color of the thermochromic coloring agent to a second and different color.

According to the first aspect, the vehicle may also include a heating source between the fluid source and the flow path that is configured to heat the fluid as it flows from the fluid source to the flow path; and a cooling source between the fluid source and the flow path that is configured to cool the fluid as it flows from the fluid source to the flow path.

According to the first aspect, the vehicle may also include a heater line that carries the fluid from the fluid source to the heating source and to the flow path; a first valve configured to permit and prevent the fluid to flow from the fluid source to the heater line; and a first pump that when the first valve is open is configured to draw the fluid from the fluid source to the heater line and to the flow path, wherein each of the first valve and the first pump are configured to communicate with the master controller.

According to the first aspect, the vehicle may also include a cooler line that carries the fluid from the fluid source to the cooling source and to the flow path; a second valve configured to permit and prevent the fluid to flow from the fluid source to the cooling line; and a second pump that when the second valve is open is configured to draw the fluid from the fluid source to the cooling line and to the flow path, wherein each of the second valve and the second pump are configured to communicate with the master controller.

According to the first aspect, based on analysis by the master controller of the signals indicative of the physiologic condition of the driver of the vehicle generated by the monitoring device, the master controller is configured to determine whether to heat or cool the fluid, and based on the determination whether to heat or cool the fluid, the master controller is configured to control each of the first valve, second valve, first pump, and second pump to control whether the fluid enters the heater line or the cooler line before entering the flow path.

According to the first aspect, the vehicle may also include a temperature sensor upstream from the flow path for generating signals indicative of a temperature of the fluid.

According to the first aspect, the heating source is an exhaust gas of the vehicle, and the cooling source is an HVAC system of the vehicle.

According to the first aspect, the fluid includes a ferrofluid.

According to the first aspect, the physiologic condition monitoring device is incorporated into a steering wheel of the vehicle in the form of a light guide that emits infrared light to detect volumetric variations of blood circulation of the driver of the vehicle.

According to the first aspect, the vehicle may also include an infotainment system including an infotainment system electronic control unit in communication with each of the monitoring device and the master controller.

According to the first aspect, the physiologic condition monitoring device may be smart watch or bracelet that communicates with the infotainment system electronic control unit, and upon receipt of the signals indicative of the physiologic condition of the driver of the vehicle generated by the smart watch or bracelet, the infotainment system electronic control unit communicates the signals to the master controller for analysis.

According to the first aspect, the backing layer is formed of a magnetizable material.

According to the first aspect, the vehicle may also include a current or voltage source in communication with the master controller, and configured to provide a current or voltage to the backing layer.

According to the first aspect, upon receipt of an instruction from the master controller, the current or voltage source provides the current or voltage to the backing layer to magnetize the backing layer.

According to the first aspect, the fluid is a ferrofluid and magnetization of the backing layer halts flow of the ferrofluid in the flow path to heat or cool the thermochromic coloring agent.

According to a second aspect of the present disclosure, there is provided a method for influencing a physiologic condition of a driver of a vehicle that includes at least one interior panel that is formed of a material including a thermochromic coloring agent, wherein the method includes generating signals indicative of at least one of volumetric variations of blood circulation and breathing rate of the driver of the vehicle with a physiologic monitoring device; communicating the signals from the monitoring device to a master electronic control unit of the vehicle; analyzing, by the master electronic control unit, the signals indicative of at least one of volumetric variations of blood circulation and breathing rate of the driver of the vehicle; and based on the analysis of the signals by the master electronic control unit, conducting at least one of heating and cooling of a fluid that is located proximate the thermochromic coloring agent of the interior panel to change a temperature of the thermochromic coloring agent via the fluid in order to change a first color of the thermochromic coloring agent to a second and different color to influence the physiologic condition of the driver of the vehicle.

According to the second aspect, the physiologic condition monitoring device is smart watch or bracelet worn by the driver of the vehicle.

According to the second aspect, the method may also include communicating the signals from the monitoring device to an infotainment electronic control unit of an infotainment system of the vehicle, and the communicating the signals from the monitoring device to a master electronic control unit of the vehicle includes communicating the signals received by the infotainment electronic control unit to the master electronic control unit.

According to the second aspect, the conducting at least one of heating and cooling of the fluid that is located proximate the thermochromic coloring agent includes heating the fluid with an engine exhaust of the vehicle and cooling the fluid with an HVAC system of the vehicle.

According to the second aspect, the fluid is a ferrofluid.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

FIG. 5 illustrates the temperature and color of a thermochromic material that may be incorporated into an interior panel illustrated in FIG. 3.

Corresponding reference numerals indicate corresponding parts throughout the several views of the drawings.

DETAILED DESCRIPTION

Figure 1:
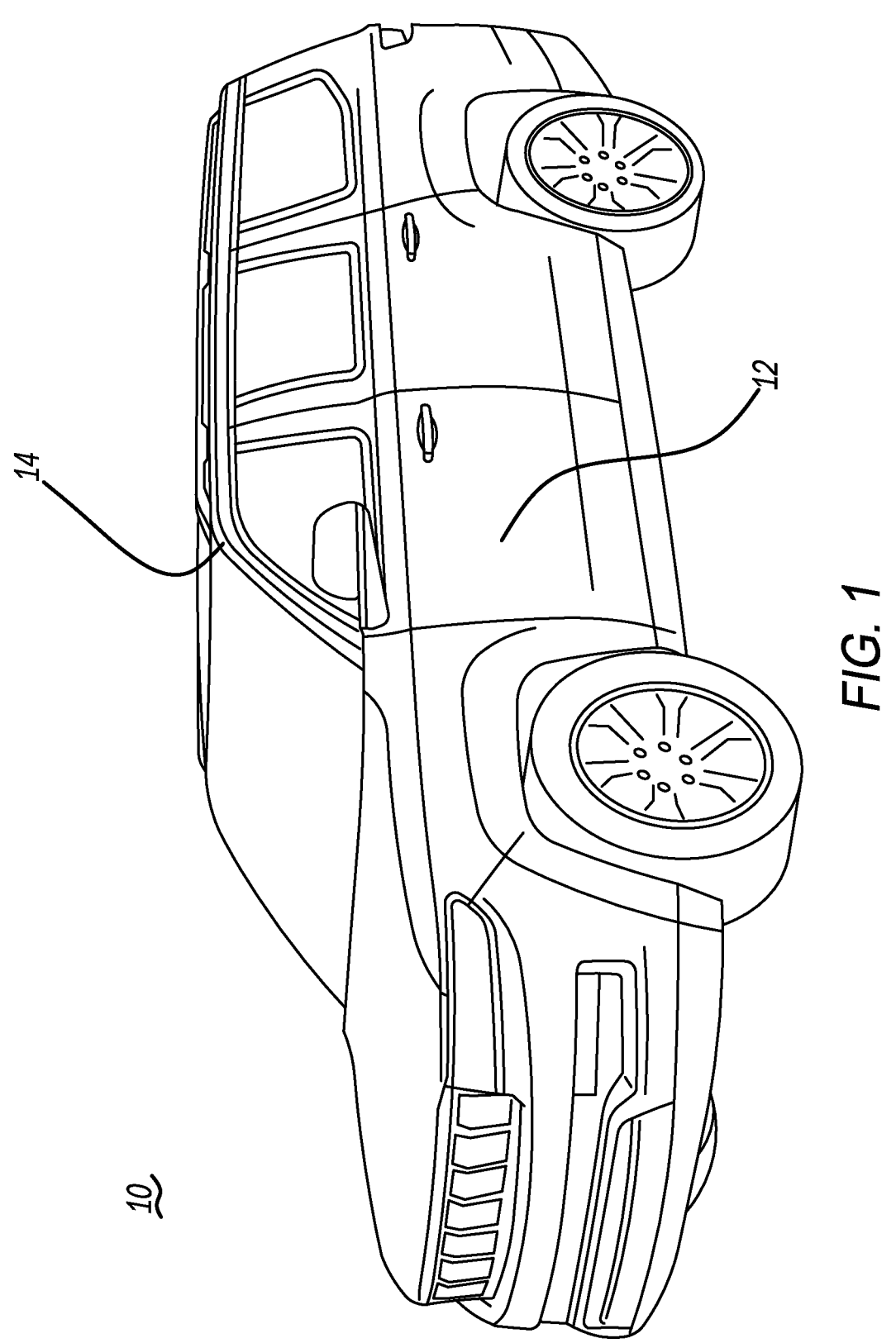
FIG. 1 is a perspective view of an example vehicle according to a principle of the present disclosure.

Example embodiments will now be described more fully with reference to the accompanying drawings. The example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 2:
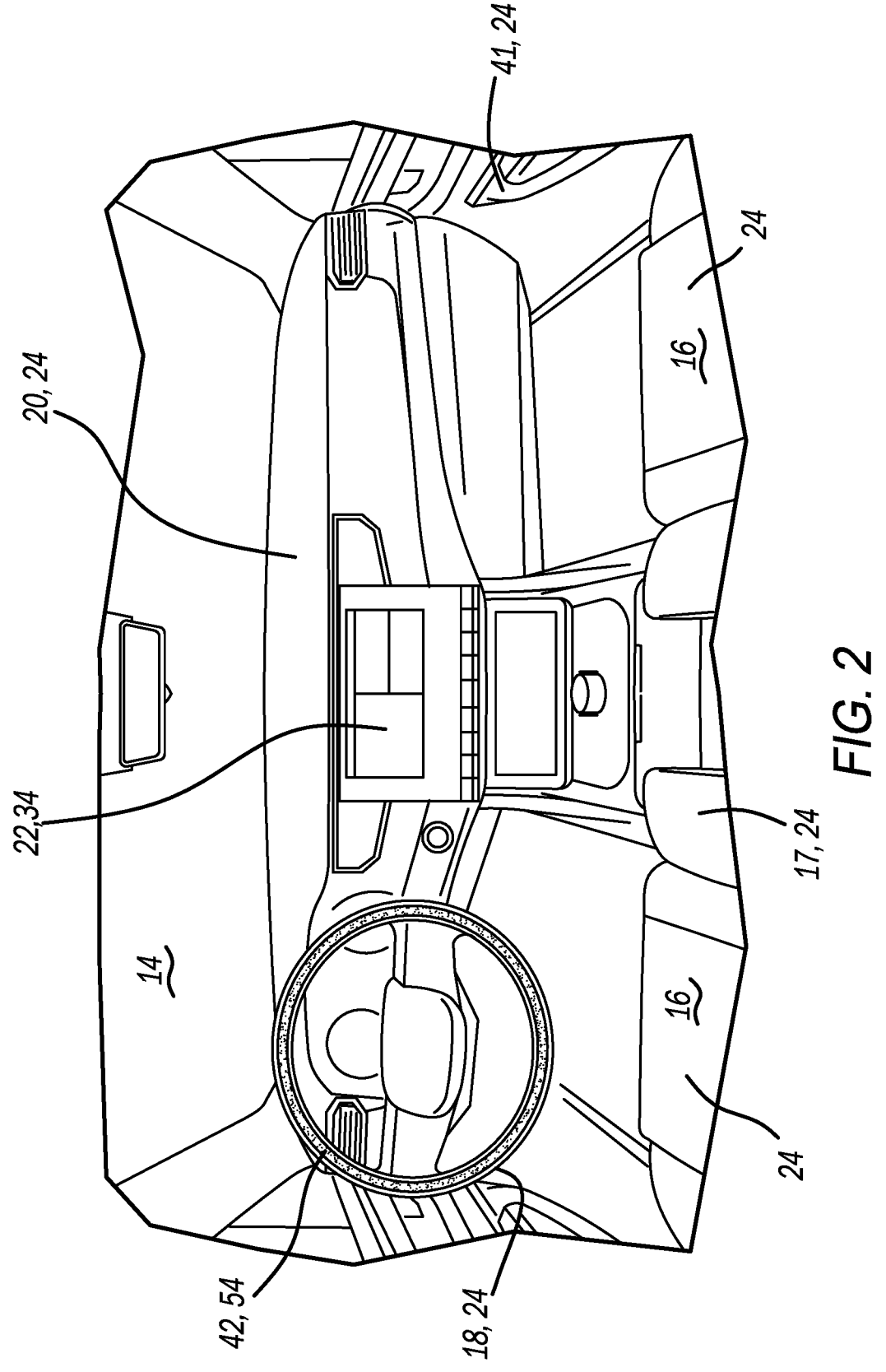
FIG. 2 is a perspective view of an example cabin of the example vehicle illustrated in FIG. 1.

FIGS. 1 and 2 illustrates an example vehicle 10 according to the present disclosure. Vehicle 10 includes a body 12 defining a cabin 14 that, as shown in FIG. 2, may include a plurality of seats 16, a center console 17, a steering wheel 18, dashboard 20, vehicle infotainment system 22, and a plurality of interior panels 24.

Figure 3:
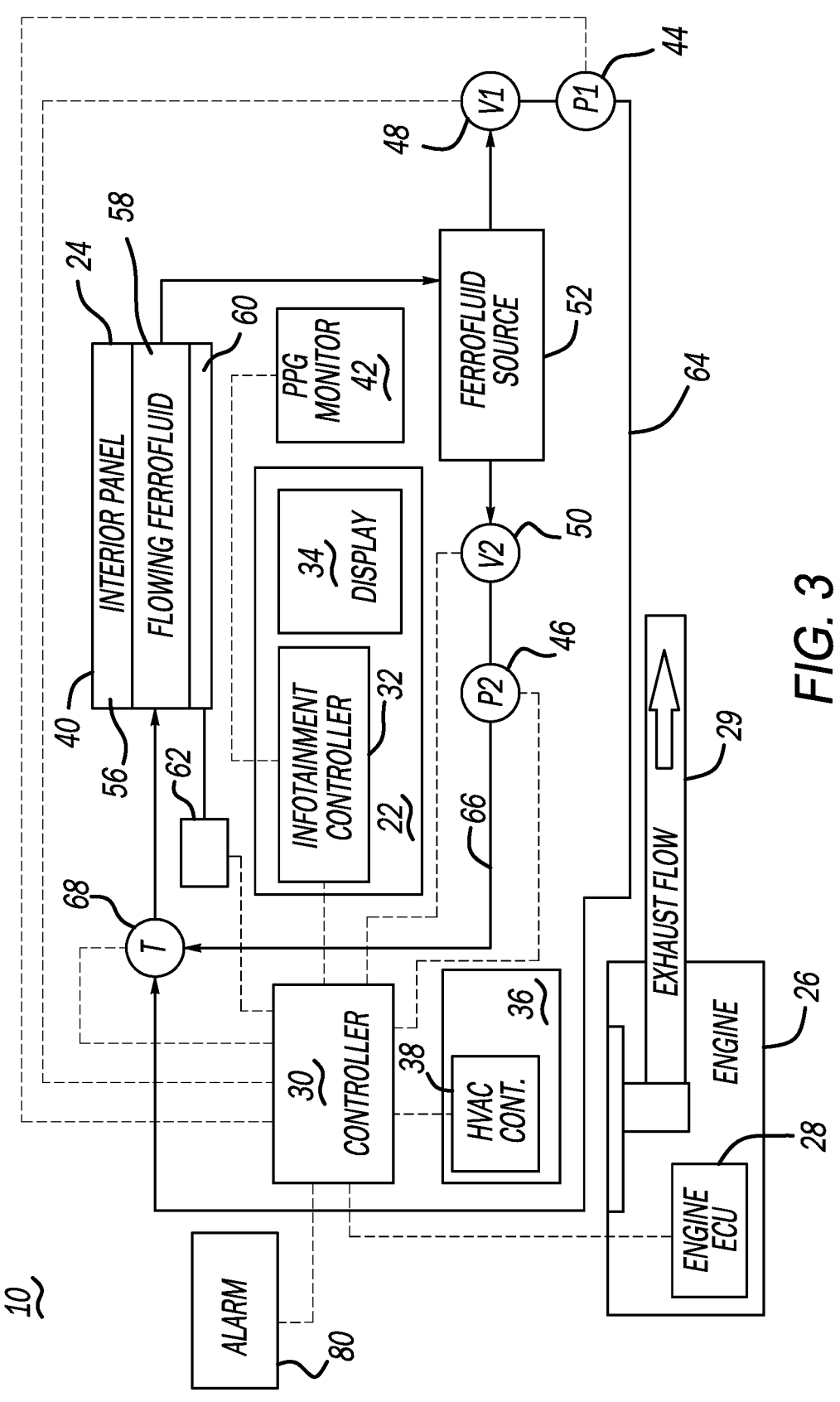
FIG. 3 is a schematic representation of the example vehicle illustrated in FIG. 1.

Vehicle 10 may be any vehicle known to one skilled in the art, including but not limited to a passenger car or truck, a train, a boat, an airplane, a piece of construction equipment such as, for example, an excavator, or any other vehicle. Regardless of the type of vehicle 10, as best shown in FIG. 3, the vehicle 10 includes an engine 26 having an engine electronic control unit 28 and exhaust outlet 29, a master electronic control unit (ECU) 30 that is configured to communicate with various systems of the vehicle 10 including, for example, engine 26, infotainment system 22 that may include an infotainment system control unit 32 and a display 34, which may include a touch screen graphic user interface (GUI). Other vehicle systems that may communicate with master ECU 30 include a vehicle HVAC system 36 having a HVAC control unit 38 that, based on instructions received from master ECU 30 may be used to heat and/or cool cabin 14 of vehicle 10, as is known in the art.

More specifically, an operator of vehicle 10 may input a climate control instruction to GUI of display 34, which is transmitted by infotainment control unit 32 to master ECU 30. Based on the climate control input received by master ECU 30 from infotainment control unit 32, master ECU 30 can then send an instruction to HVAC control unit 38 to either heat or cool the cabin 14 of vehicle 10. HVAC system 36 is only schematically illustrated in FIG. 3 and various features thereof are not illustrated including but not limited to heat exchangers, inlet and outlet lines that communicate with the heat exchangers, and various valves that control the flow of coolant and/or refrigerant throughout HVAC system 36.

As noted above, vehicle 10 includes interior panels 24 that may have an outer surface 40 that, although not illustrated in FIG. 3, may be textured. Interior panels 24 may be, for example, part of dashboard 20, a material that defines an exterior surface of vehicle seats 16 or center console 17, and a material that defines an exterior surface of steering wheel 18. Other "interior panels" 24 include an interior roof panel (not shown), an interior door panel 41, a vehicle floor panel (not shown), or any other panel that may be located within the cabin 14 of the vehicle 10. According to the present disclosure, various interior panels 24 may be formed to include a thermochromic material or coloring agent that when heated and/or cooled is configured to change from one color to another color, as will be described in more detail later. The panels 24 may each include the same thermochromic material, the panels 24 may each include a different thermochromic material, or the panels 24 may include various portions that each include a different thermochromic material.

Color can be a powerful communication tool and can be used to signal action, influence mood, and even influence physiological reactions. Certain colors have been associated with physiological changes, including increased blood pressure, increased metabolism, and eyestrain. In addition, color can be used as a tool to relieve stress and increase happiness. For example, the color blue can be used to manage stress because the color blue may be perceived as peaceful, calm, and gentle; the color green can be perceived as comforting and refreshing, which can diffuse anxiety; the color red can be perceived as aggressive and vibrant, which can stimulate enthusiasm; the color pink can promote tranquility and peacefulness; and the color yellow can generate feelings of liveliness and energetic. With the above in mind, the interior panel 24 including the thermochromic material or colorant can be heated and/or cooled to control he color that is emitted by the thermochromic material to stimulate or soothe the driver of vehicle 10 based on the physiological condition of the driver.

To monitor the physiological condition of the driver of vehicle 10, as shown in FIG. 3, vehicle 10 includes a physiologic condition monitoring device 42 that is configured to utilize photoplethysmography to detect blood volume changes in a microvascular bed of tissue. This technique is often used for heart-rate monitoring purposes. Such a device may be incorporated, for example, into the steering wheel 18 of vehicle 10 such that when the driver grasps the steering wheel, a signal indicative of blood volume changes in the driver's fingers or hand can be transmitted by monitoring device 42 directly to master ECU 30 (not shown in FIG. 3) or to infotainment control device 32, which can then direct the signal to master ECU 30.

Then, based on the signal indicative of the blood volume changes, the master ECU 30 may communicate signals to various pumps 44, 46 and valves 48, 50 that control the flow of a thermally stimulating fluid from a thermally stimulating fluid source 52 that is used to thermally stimulate the thermochromic material of the interior panel 24 such that the color of the thermographic material and interior panel 24 can change to another color that can either stimulate or soothe the driver. The thermally stimulating fluid from fluid source 52 can be directed using pumps 44, 46 and valves 48, 50 to either a heat source for heating the thermally stimulating fluid or a cooling source for cooling the thermally stimulating fluid. In the illustrated example embodiment of FIG. 3, an example cooling source may be HVAC system 36 and an example heating source may be the flow of exhaust through exhaust outlet 29, which will be described in more detail later. Other cooling and heating sources, however, are contemplated including heater cores (not shown), air coolers (not shown), or other sources of cooling and heating that may be commonly used in vehicle 10 as known to one skilled in the art. Although only a single fluid source 52 is illustrated in FIG. 3, it should be understood that a plurality of fluid sources 52 can be used, with each interior panel 24 having a dedicated fluid source 52.

Photoplethysmography, known most commonly as PPG, utilizes an infrared light to measure the volumetric variations of blood circulation. Thus, if monitoring device 42 is incorporated into steering wheel 18, steering wheel 18 may include a light guide 54 (shown schematically in FIG. 2) that travels about a circumference of steering wheel 18 that emits infrared light such that when the driver grasps steering wheel 18, signals indicative of volumetric variations in blood circulation may be transmitted to master ECU 30.

Alternatively, monitoring device 42 may be a smart watch or bracelet worn by the driver of vehicle 10. In such an example embodiment, the driver's heart rate or volumetric variations of blood circulation that may be detected by monitoring device 42 can be transmitted from monitoring device 42 to infotainment control unit 32, which then transmits the signal to master ECU 30. Master ECU 30 may then communicate the appropriate signals to the pumps 44, 46 and valves 48, 50 to control the flow of the thermally stimulating fluid from fluid source 52 to either the heat source or cooling source. If monitoring device 42 is a smart watch or bracelet, the smart watch or bracelet may communicate wirelessly with infotainment control device 32 via communication protocols known to one skilled in the art such as, for example, Bluetooth®.

Figure 4:
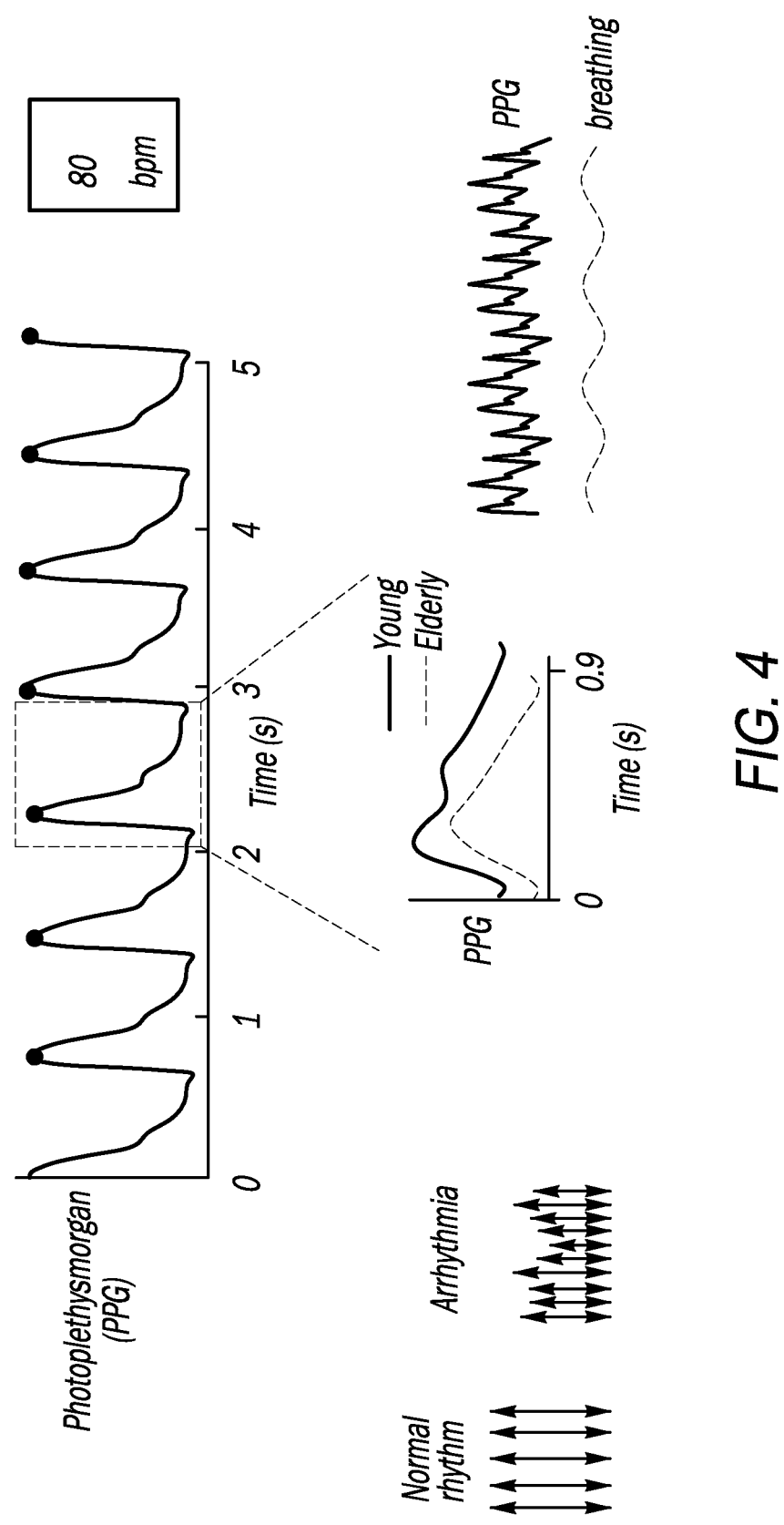
FIG. 4 illustrates photoplethysmography data obtained by a physiologic monitoring device illustrated in FIG. 3.

Other physiologic conditions that may be monitored and communicated to master ECU 30 include breathing rate, which can indicate stress, anxiety, and the like. If such a condition is to be detected by vehicle 10, monitoring device 42 may be the smart watch or bracelet, or incorporated into the driver seat 16 of vehicle 10 in the form of a pressure sensor (not shown) that can detect the driver's breathing rate. Examples of a driver's heart rate and breathing rate that may be detected using PPG by monitoring device 28 and ultimately communicated to ECU 26 are illustrated in FIG. 4.

As noted above, based on the PPG information transmitted via monitoring device 42 to master ECU 30, the various interior panels 24 that are formed to include a thermochromic material are configured to change from one color to another color that may influence the driver's emotional state (e.g., stimulate or soothe the driver). The interior panel 24 illustrated in FIG. 3 includes an exterior or decorative outer layer 56 that may be formed of, for example, a molded-in-color (MIC) polymeric material, a polymeric vinyl material, or any other polymeric trim material known to one skilled in the art. The polymeric material of outer layer 56 includes a thermochromic material that provides the interior panel 24 with a first color under ambient conditions (e.g., the thermochromic material is red at 60 degrees C.) and a second color (e.g., orange or yellow) when heated to a temperature greater than 60 degrees C. The change in color from red to orange or yellow at various temperatures greater than 60 degrees C. is shown in FIG. 5. Other colors are contemplated. For example, a thermochromic material that is blue at ambient conditions (e.g., 60 degrees C.) and green when heated to temperatures greater than 60 degrees C. The color change is dependent on the thermochromic material selected to be incorporated into the outer layer 56.

Example thermochromic materials include, for example, dual type thermochromic pigments and single type thermochromic pigments. "Daehyun TCP D. Blue" is an example dual type thermochromic pigment where the pigment is black at ambient temperature and a second color appears at temperatures above 50° C. Single type thermochromic pigments are those that are colorless at ambient temperature and the second color appears when the temperature of the thermochromic material reaches 65° C., and the second color could be red, green, yellow, or blue. When the thermochromic material is colorless at ambient temperature, it should be understood that the initial color of the interior panel 24 before the thermochromic material is activated will be determined by the color of the material (e.g., polypropylene or other material) that forms the outer layer 56 of interior panel 24. The thermochromic materials are added to the mixture of materials (e.g., polymer, additional coloring agents, filler, and the like) that are used to form outer layer 56 and compounded together.

As shown in FIG. 3, the interior panel 24 also includes a flow path 58 for the thermally stimulating fluid traveling from fluid source 52. In the illustrated embodiment, the thermally stimulating fluid may be a ferrofluid, which is a colloidal liquid that includes nanoscale ferromagnetic or ferrimagnetic particles. Interior panel 24 also includes a backing layer 60 that, in combination with outer layer 56, sandwiches the flow path 58. Backing layer 60 may be formed of a material that, when applied with a current or voltage, may be magnetized. To provide the current or voltage to backing layer 60, vehicle 10 may include a current/voltage source 62 such as, for example, a vehicle battery that is in communication with master controller 30.

Upon receipt of an instruction from master controller 30, current/voltage source 62 may communicate the current/voltage to backing layer 60 to magnetize the backing layer 60 and attract the magnetic particles contained in the ferrofluid (i.e., halt or "freeze" the flow of the ferrofluid in flow path 58). Because the ferrofluid is either heated or cooled using HVAC 36 or the engine exhaust traveling through exhaust outlet 29, the heated or cooled ferrofluid that is held in flow path 58 will thermally stimulate the thermochromic material of outer layer 58, at which time the thermochromic material contained in outer layer 58 can change from one color to another.

As noted above, the flow of the ferrofluid from fluid source 52 to flow path 58 is controlled using pumps 44, 46, and valves 48, 50. A first valve 48 and a first pump 44 can draw the ferrofluid from fluid source 52 and direct the ferrofluid through a heater line 64 that travels adjacent to and along exhaust outlet 29. A second pump 46 and a second valve 50 can draw the ferrofluid from fluid source 52 and direct the ferrofluid through a cooler line 66 that travels adjacent to and along HVAC system 36. If the ferrofluid is to be heated, second valve 50 is closed and second pump 46 is prevented from operating. If the ferrofluid is to be cooled, first valve 48 is closed and first pump 44 is prevented from operating. Alternatively, first and second valves 48, 50 may each be open and first and second pumps 44, 46 may each be operating simultaneously to provide ferrofluid with an intermediate temperature that is either slightly heated or slightly cooled. The important aspect to keep in mind is that the system is designed such that thermochromic particles change from one color to another color based on the PPG signals of the driver of the vehicle 10 received and communicated by monitoring device 42, and the change from one color to another color by the thermochromic material is dependent on temperature. Accordingly, through operation of pumps 44, 46 and valves 48, 50, the temperature of the ferrofluid can be strictly controlled, which in turn can control the thermochromic material changing from one color to another color to change the appearance (i.e., color) of the outer layer 56 of the interior panel 24.

If the ferrofluid is to be heated, master ECU opens first valve 48 and permits first pump 46 to operate. Before actuating first pump 44 and opening first valve 46, master ECU 30 may prevent second pump 46 from operating and close second valve 50. As the ferrofluid is drawn by first pump 44 through first valve 46 and into heater line 64 that extends adjacent to and along exhaust outlet 29, the hot exhaust gases produced by engine 26 will heat the ferrofluid in heater line 64. The amount of heating provided by the hot exhaust to the heater line 64 can be controlled by controlling the speed of first pump 44 (i.e., fluid flowing at a greater velocity through heater line 64 will not be heated as much as a fluid flowing at slower velocity through heater line 64). A temperature of the ferrofluid can be monitored by a temperature sensor 68, which communicates with master ECU 30. Based on signal indicative of a temperature of the ferrofluid received by master ECU 30, master ECU 30 can alter the speed of first pump 44 accordingly.

After the ferrofluid is heated to the desired temperature (e.g., 85 degrees C.), heater line 64 carries the heated ferrofluid to flow path 58. Once the heated ferrofluid is located in flow path 56, master ECU 30 can instruct current/voltage source 62 to magnetize backing layer 60 to "freeze" the heated ferrofluid in flow path 58 to thermally stimulate the thermochromic material of outer layer 56, at which time the thermochromic material will change in color from, for example, red to dark yellow and change the appearance of interior panel 24. The change in color may be instantaneous or gradual. Preferably, in order to result in a physiological response by the driver of vehicle 10, the change is instantaneous. After the thermochromic material changes in color, or after a predetermined amount of time has elapsed, master controller 30 instructions current/voltage source 62 to cease applying the current or voltage to backing layer 60. At this time, the attraction between the magnetic particles of the ferrofluid and the backing layer 60 ends and the ferrofluid is free to resume flow through flow path 58 back to fluid source 52 where the process may repeat.

If the ferrofluid is to be cooled, master ECU opens second valve 50 and permits second pump 46 to operate. Before actuating second pump 46 and opening second valve 50, master ECU 30 can prevent first pump 44 from operating and close first valve 48. As the ferrofluid is drawn by second pump 46 through second valve 50 and into cooler line 66 that extends adjacent to and along HVAC 36, the refrigerant carried by HVAC 36 will cool the ferrofluid in cooler line 66. The amount of cooling provided by the refrigerant to the cooler line 66 can be controlled by controlling the speed of second pump 46 (i.e., fluid flowing at a greater velocity through cooler line 66 will not be cooled as much as a fluid flowing at slower velocity through cooler line 66). A temperature of the ferrofluid can be monitored by temperature sensor 68, which communicates with master ECU 30. Based on signal indicative of a temperature of the ferrofluid received by master ECU 30, master ECU 30 can alter the speed of second pump 46 accordingly.

After the ferrofluid is cooled, cooler line 66 carries the cooled ferrofluid to flow path 58. Once the cooled ferrofluid is located in flow path 56, master ECU 30 can instruct current/voltage source 62 to magnetize backing layer 60 to "freeze" the cooled ferrofluid in flow path 58 to thermally stimulate the thermochromic material of outer layer 56, at which time the thermochromic material will change in color from, for example, dark yellow to red and change the appearance of interior panel 24. Similar to when the ferrofluid is heated, the change in color may be instantaneous or gradual. Preferably, in order to result in a physiological response by the driver of vehicle 10, the change is instantaneous. After the thermochromic material changes in color, or after a predetermined amount of time has elapsed, master controller 30 instructions current/voltage source 62 to cease applying the current or voltage to backing layer 60. At this time, the attraction between the magnetic particles of the ferrofluid and the backing layer 60 ends and the ferrofluid is free to resume flow through flow path 58 back to fluid source 52 where the process may repeat.

Figure 6:
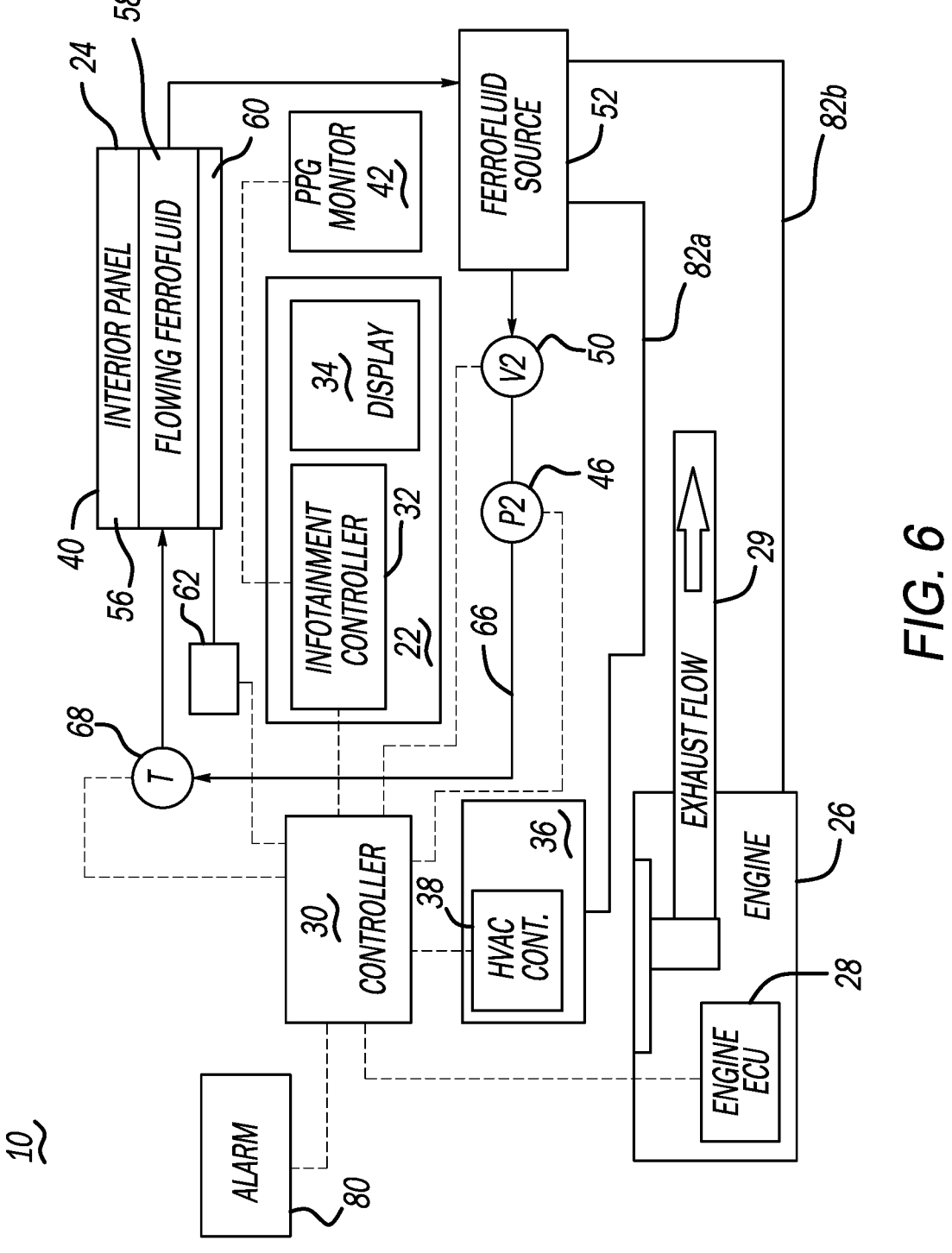
FIG. 6 is another schematic representation of the example vehicle illustrated in FIG. 1.

While the above-described configuration uses heater lines 64 and cooling lines 66 to heat/cool the ferrofluid, it should be understood that these features and first valve 48 and first pump 44 can be omitted. More specifically, referring to FIG. 6, an alternative configuration for heating and/or cooling the thermally stimulating fluid is shown. As can be seen in FIG. 6, the source 52 of thermally stimulating fluid may be heated or cooled via refrigerant lines 82a and 82b that connect HVAC 36 and engine 26. Once the thermally stimulating fluid is heated and/or cooled at source 52, the thermally stimulating fluid can be drawn by pump 46 through valve 50 and communicated to pathway 58. More specifically, the refrigerant carried by refrigerant lines 82a, 82b can be either cooled or heated by HVAC 36 and/or engine 26 and communicated to source 52 to heat and/or cool the thermally stimulating fluid located therein. After the thermally stimulating fluid has been heated and/or cooled to the desired temperature, the fluid can be directed to pathway 56 using pump 46. Although not shown in FIG. 6, it should be understood that additional pumps can cause the refrigerant to flow from HVAC 36 and/or engine 26 to source 52. Moreover, while not illustrated in FIG. 6, it should be understood that return lines that can circulate the refrigerant located in lines 82a, 82b between source 52 and either HVAC 36 or engine 26 may also be present.

Now description of how the physiologic characteristics of a driver of vehicle 10 can be changed in response to photoplethysmography (PPG) data obtained from the driver 10 with monitoring device 42 will be described. For ease of description, the following example is directed to a case where driver 10 is drowsy and the color currently being exhibited by the thermochromic material of interior panels 24 is light red or pink, which is a color that promotes tranquility and peace.

While operating vehicle 10, the PPG data of driver is monitored with monitoring device 42 and communicated to infotainment controller 32, which then transmits the same data to master ECU 30. Upon receipt by master ECU 30 of the PPG data, the master controller 30 is configured to analyze the PPG data (through, e.g., a look-up table stored in a RAM or ROM memory that may be part of master ECU 30) and determine the physiologic characteristics of the driver including whether the driver is drowsy or experiencing emotional stress, anxiety, or nervousness. For example, the master ECU 30 can analyze the PPG data and determine whether the driver has a normal heart rhythm or an arrhythmia or light or heavy breathing (see FIG. 4). As noted above, in this case, the master ECU 30 will analyze the PPG data and determined that the driver is drowsy and needs to be stimulated.

In response to determining that the driver is drowsy and needs to be stimulated, master ECU 30 will determine that the color of the thermochromic material of the interior panels 24 needs to change from pink to yellow, which is a color that promotes liveliness and energy. As shown in FIG. 5, to change the color of the thermochromic material from light red to yellow, the thermochromic material needs to be heated to a temperature of about 75 to 85 degrees C. Accordingly, master ECU 30 will communicate instructions to first and second valves 48, 50 and first and second pumps 44, 46 that prevent the ferrofluid contained in fluid source 52 from entering cooler line 66, and permit the ferrofluid contained in fluid course 52 to enter heater line 64. That is, second valve 50 will be closed and second pump 46 will not be operating, and first valve 48 will be open and first pump 44 will be operating to draw the ferrofluid from fluid source 52 into heater line 64.

In addition, master ECU 30 will control the speed of first pump 44 such that ferrofluid can be heated to a temperature in the range of 75 degrees C. to 85 degrees C. by the hot exhaust gases carried by exhaust outlet 29, based on signals indicative of temperature received by master ECU 30 from temperature sensor 68. Once the ferrofluid is at the desired temperature for changing the color of the thermochromic material from light red or pink to yellow, master ECU 30 will instruct current/voltage source 62 to transmit a current or voltage to backing layer 60. At this time, backing layer 60 is magnetized to attract the magnetic particles of the ferrofluid and "freeze" the ferrofluid in the flow path 58 and permit the ferrofluid to heat the thermochromic material of the outer layer 56 of interior panel 24 and permit the thermochromic material to change in color from light red or pink to yellow.

After the thermochromic material changes in color to yellow, the driver should feel enlivened and energized and exhibit a corresponding PPG response. Monitoring device 42 continues to transmit PPG data to infotainment controller 32, which transmits the PPG data to master ECU 30 for analysis. If the PPG data of driver is indicative of the driver feeling enlivened and energized, master ECU 30 may continue to operate first pump 44 to continue to heat the ferrofluid and maintain the yellow color of the thermochromic material for a predetermined amount of time (e.g., until operation of vehicle 10 is stopped, which can, for example, be based on a signal received from engine ECU 28 that engine 26 is no longer running). In this manner, the physiologic characteristics of the driver can be influenced by the change in color of the thermochromic material of the interior panels 24.

A similar method can be used to soothe a driver of vehicle 10. That is, if the driver is agitated or experiencing stress and/or anxiety, the interior panels 24 can be heated and/or cooled to change a color of the panels 24 to a color that is more soothing (e.g., be changed to a green or blue color).

While changes in color are an effective way to stimulate or soothe the driver of vehicle 10, it should be understood that in some cases the change in color of interior panels 24 may not be effective. Accordingly, vehicle 10 may be provided with an alarm 80. If master ECU 30 determines from the PPG data that the driver is, for example, still drowsy after the color change, master ECU 30 may instruct the alarm 80 to generate sounds and/or flashing lights that can attempt to cure the drowsiness of the driver of vehicle 10.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A vehicle including a body defining a vehicle cabin, the vehicle comprising:
   a plurality of interior panels located in the vehicle cabin that include an outer decorative layer formed of a material that includes a thermochromic coloring agent, a backing layer, and a flow path sandwiched between the outer decorative layer and the backing layer;
   a physiologic condition monitoring device configured to generate signals indicative of various physiologic conditions of a driver of the vehicle;
   a master controller in communication with the monitoring device that is configured to receive and analyze the signals generated by the monitoring device; and
   a fluid source in fluid communication with the flow path, the fluid source having a fluid that is configured to flow between the fluid source and the flow path,
   wherein based on analysis by the master controller of the signals indicative of the physiologic condition of the driver of the vehicle generated by the monitoring device, the fluid in the flow path is configured to selectively heat and cool the thermochromic coloring agent to change a first color of the thermochromic coloring agent to a second and different color, and
   wherein the fluid includes a ferrofluid.

2. The vehicle according to claim 1, further comprising:
   a heating source between the fluid source and the flow path that is configured to heat the fluid as it flows from the fluid source to the flow path; and
   a cooling source between the fluid source and the flow path that is configured to cool the fluid as it flows from the fluid source to the flow path.

3. The vehicle according to claim 2, further comprising:
   a heater line that carries the fluid from the fluid source to the heating source and to the flow path;
   a first valve configured to permit and prevent the fluid to flow from the fluid source to the heater line; and
   a first pump that when the first valve is open is configured to draw the fluid from the fluid source to the heater line and to the flow path,
   wherein each of the first valve and the first pump are configured to communicate with the master controller.

4. The vehicle according to claim 3, further comprising:
   a cooler line that carries the fluid from the fluid source to the cooling source and to the flow path;
   a second valve configured to permit and prevent the fluid to flow from the fluid source to the cooling line; and
   a second pump that when the second valve is open is configured to draw the fluid from the fluid source to the cooling line and to the flow path,
   wherein each of the second valve and the second pump are configured to communicate with the master controller.

5. The vehicle according to claim 4, wherein based on analysis by the master controller of the signals indicative of the physiologic condition of the driver of the vehicle generated by the monitoring device, the master controller is configured to determine whether to heat or cool the fluid, and based on the determination whether to heat or cool the fluid, the master controller is configured to control each of the first valve, second valve, first pump, and second pump to control whether the fluid enters the heater line or the cooler line before entering the flow path.

6. The vehicle according to claim 4, further comprising a temperature sensor upstream from the flow path for generating signals indicative of a temperature of the fluid.

7. The vehicle according to claim 2, wherein the heating source is an exhaust gas of the vehicle, and the cooling source is an HVAC system of the vehicle.

8. The vehicle according to claim 1, wherein the physiologic condition monitoring device is incorporated into a steering wheel of the vehicle in the form of a light guide that emits infrared light to detect volumetric variations of blood circulation of the driver of the vehicle.

9. The vehicle according to claim 1, further comprising an infotainment system including an infotainment system electronic control unit in communication with each of the monitoring device and the master controller.

10. The vehicle according to claim 9, wherein the physiologic condition monitoring device is smart watch or bracelet that communicates with the infotainment system electronic control unit, and upon receipt of the signals indicative of the physiologic condition of the driver of the vehicle generated by the smart watch or bracelet, the infotainment system electronic control unit communicates the signals to the master controller for analysis.

11. The vehicle according to claim 1, wherein the backing layer is formed of a magnetizable material.

12. The vehicle according to claim 11, further comprising a current or voltage source in communication with the master controller and configured to provide a current or voltage to the backing layer.

13. The vehicle according to claim 12, wherein upon receipt of an instruction from the master controller, the current or voltage source provides the current or voltage to the backing layer to magnetize the backing layer.

14. The vehicle according to claim 13, wherein the fluid is a ferrofluid and magnetization of the backing layer halts flow of the ferrofluid in the flow path to heat or cool the thermochromic coloring agent.

15. A method for influencing a physiologic condition of a driver of a vehicle that includes at least one interior panel that is formed of a material including a thermochromic coloring agent, comprising:

generating signals indicative of at least one of volumetric variations of blood circulation and breathing rate of the driver of the vehicle with a physiologic monitoring device;

communicating the signals from the monitoring device to a master electronic control unit of the vehicle;

analyzing, by the master electronic control unit, the signals indicative of at least one of volumetric variations of blood circulation and breathing rate of the driver of the vehicle; and based on the analysis of the signals by the master electronic control unit, conducting at least one of heating and cooling of a fluid that is located proximate the thermochromic coloring agent of the interior panel to change a temperature of the thermochromic coloring agent via the fluid in order to change a first color of the thermochromic coloring agent to a second and different color to influence the physiologic condition of the driver of the vehicle, wherein the fluid is a ferrofluid.

16. The method according to claim 15, wherein the physiologic condition monitoring device is smart watch or bracelet worn by the driver of the vehicle.

17. The method according to claim 16, further comprising communicating the signals from the monitoring device to an infotainment electronic control unit of an infotainment system of the vehicle, and the communicating the signals from the monitoring device to a master electronic control unit of the vehicle includes communicating the signals received by the infotainment electronic control unit to the master electronic control unit.

18. The method according to claim 15, wherein the conducting at least one of heating and cooling of the fluid that is located proximate the thermochromic coloring agent includes heating the fluid with an engine exhaust of the vehicle and cooling the fluid with an HVAC system of the vehicle.

* * * * *